US011609196B2

(12) United States Patent
Sale et al.

(10) Patent No.: US 11,609,196 B2
(45) Date of Patent: Mar. 21, 2023

(54) DEVICES AND METHODS FOR MEASURING NATURAL SOURCE ZONE DEPLETION RATES

(71) Applicant: COLORADO STATE UNIVERSITY RESEARCH FOUNDATION, Fort Collins, CO (US)

(72) Inventors: Thomas C. Sale, Bellvue, CO (US); Kayvan Karimi Askarani, Fort Collins, CO (US)

(73) Assignee: COLORADO STATE UNIVERSITY RESEARCH FOUNDATION, Fort Collins, CO (US)

(*) Notice: Subject to any disclaimer, the term of this patent is extended or adjusted under 35 U.S.C. 154(b) by 379 days.

(21) Appl. No.: 16/874,258

(22) Filed: May 14, 2020

(65) Prior Publication Data

US 2020/0363359 A1 Nov. 19, 2020

Related U.S. Application Data

(60) Provisional application No. 62/849,224, filed on May 17, 2019.

(51) Int. Cl.
*G01N 25/00* (2006.01)
*G01N 25/48* (2006.01)
*G01N 33/24* (2006.01)
*G01K 3/10* (2006.01)

(52) U.S. Cl.
CPC .......... *G01N 25/4866* (2013.01); *G01K 3/10* (2013.01); *G01N 25/4853* (2013.01); *G01N 33/24* (2013.01)

(58) Field of Classification Search
CPC combination set(s) only.
See application file for complete search history.

(56) References Cited

U.S. PATENT DOCUMENTS

| 10,094,719 B2 | 10/2018 | Sale et al. |
| 10,113,990 B2 | 10/2018 | Burge et al. |
| 10,746,718 B2 | 8/2020 | Zimbron |
| 2013/0087327 A1* | 4/2013 | Nguyen ............... E21B 47/07 166/250.01 |

(Continued)

*Primary Examiner* — Lisa M Caputo
*Assistant Examiner* — Nasir U. Ahmed
(74) *Attorney, Agent, or Firm* — Polsinelli PC

(57) ABSTRACT

A subsurface monitoring system and method is provided for measuring a rate of change in an amount of a reactive material within a subsurface formation using measurements of thermal parameters at one or more positions within the subsurface without the need for background correction which may lead erroneous calculations and require additional monitoring equipment. The measured thermal parameters may be used to determine the heat generated by the degradation of the reactive material. The method may include measuring a first temperature near the surface of a subsurface region and a second temperature further from the surface. In some instances, an estimated location of a planar subsurface heat source/sink due to exothermic degradation reactions within the subsurface may be selected. With the derived thermal parameters and the estimated location of the subsurface heat source/sink, change rates for the reactive materials in the subsurface region may be determined or estimated.

20 Claims, 6 Drawing Sheets
(3 of 6 Drawing Sheet(s) Filed in Color)

(56) References Cited

U.S. PATENT DOCUMENTS

2015/0233773 A1\* 8/2015 Sale ...................... E21B 47/07
  374/29
2020/0116894 A1 4/2020 Sale et al.

\* cited by examiner

DEVICES AND METHODS FOR MEASURING NATURAL SOURCE ZONE DEPLETION RATES

CROSS REFERENCE TO RELATED APPLICATION

This application claims priority from U.S. provisional patent application Ser. No. 62/849,224, entitled "Single Stick Computational Algorithm" filed on May 17, 2019, the entirety of which is incorporated by reference herein.

FIELD OF THE INVENTION

This application relates to devices and methods for subsurface monitoring. In particular, this application relates to methods and devices of measuring, collecting, and analyzing subsurface temperature profiles to obtain an understanding of subsurface conditions.

BACKGROUND OF THE INVENTION

In almost every part of the world, vast amounts of petroleum have been produced, transported, refined, stored, and/or used as fuel or feedstock. Correspondingly, inadvertent releases of petroleum liquids have occurred, and large amounts of petroleum liquids have been released into soil and groundwater. An ongoing environmental challenge is managing the legacy of such anthropogenic activities that have resulted in the contamination of groundwater, surface water, soil, sediments and/or soil gas in subsurface source zones and plumes. Subsurface petroleum liquids may be referred to as light non-aqueous phase liquids (LNAPLs), and the processes constraining the extent of LNAPL bodies may be referred to as natural source zone depletion (NSZD). Source zones may be defined as saturated or unsaturated subsurface regions containing hazardous substances, pollutants, or reactive materials that may act as reservoirs that sustain a reactive material plume in groundwater, surface water, or air or may act as sources for direct exposure. These source zones may include sorbed and aqueous-phase reactive materials as well as non-aqueous reactive materials such as solids or nonaqueous phase liquids. Plumes are zones about source zones where contaminants have moved to, from source zones, via the flow of fluids and/or diffusion.

NSZD losses are part of the natural short-term biological organic carbon cycle, wherein organic carbon is introduced into shallow subsurface setting and subsequently returned to the atmosphere as gases. Initial efforts to quantify NSZD rates focused on quantifying NSZD gas fluxes. However, a common limitation of gas flux methods is that measurements are typically made over brief periods in systems where gas fluxes can be dynamic due to short-term barometric pumping and/or transient soil moisture. Further, the accuracy of gas-flux-based NSZD rates can be constrained by non-uniform gas fluxes in porous media associated with heterogeneous gas-phase diffusion coefficients and soil permeability for gases.

More recently, temperature-based approaches for quantifying LNAPL NSZD rates have been advanced. Such approaches may involve: 1) continuously measuring of vertical temperature profiles in background and LNAPL-impacted areas, 2) isolating NSZD heat from heat associated with surface heating by subtracting background temperatures from temperature in LNAPL impacted areas, 3) conduction of an energy balance to resolve NSZD energy (e.g., $W/m^2$), and 4) estimating NSZD rates by dividing NSZD energy by the estimated NSZD heat of reaction. Continuous temperature monitoring addresses issues with temporally sparse gas flux measurements and thermal properties of subsurface media are arguably far more uniform than gas-phase diffusion coefficients and soil permeability The primary limitation of published methods for transforming temperature to NSZD rates is that background correction for surface heating and cooling at LNAPL-impacted locations constrains the accuracy of reported values. Manifestations of flawed background corrections can include occasionally implausible NSZD rates in areas where there is no LNAPL, negative NSZD rates, and/or improbably large NSZD rates in area with LNAPL. Background locations dissimilar to the LNAPL-impacted locations, through time, with respect to all factors controlling surface heating and cooling including albedo, infiltration/evaporation of precipitation, and incident radiation, to name a few, may cause inaccurate measurement of temperature profiles of the monitored zone. For example, a background location with asphalt and direct sunlight is likely to yield flawed background-correction data for surface heating and cooling in an LNAPL-impacted area with direct sunlight and a natural vegetative cover.

A need exists for a robust method and devices for monitoring subsurface conditions containing hazardous substances, pollutants, or reactive materials in groundwater, surface water, or air or may act as sources for direct exposure. Such a method may be used to monitor the degree of contamination of a subsurface formation, to assess the rate of degradation of the reactive materials, resolve the areal and vertical extent of contaminants, and assess the effectiveness of remedial actions addressing subsurface contamination.

SUMMARY OF THE INVENTION

An aspect of the present disclosure may include systems and methods for monitoring subsurface conditions. In some instances, the system may include a first thermal sensor in communication with a data logger, the first thermal sensor transmitting, to the data logger, at least one obtained temperature at a first subsurface location and a second thermal sensor in communication with the data logger, the second thermal sensor transmitting, to the data logger, at least one obtained temperature at a second subsurface location below the first subsurface location. The system may also include a computing device in communication with the data logger, the computing device comprising at least one hardware processor and at least one memory to store executable instructions. When executed by the at least one processor, the executable instructions may be configured to estimate a planar location of a subsurface heating or cooling source produced by an endothermic reaction or an exothermic reaction of organic material within a subsurface formation and calculate, utilizing the least one obtained temperature at the first subsurface location and the least one obtained temperature at the second subsurface location, a first thermal parameter corresponding to an estimated rate of thermal change of a surface heating or cooling source and a second thermal parameter corresponding to an estimated rate of thermal change of the subsurface heating or cooling source based on the estimated location. The executable instructions may also be configured to convert the first thermal parameter and the second thermal parameter into a rate of change of an amount of the organic material within the subsurface formation and execute a site remedy for remediation of the subsurface formation based on the rate of change of the amount of the organic material within the subsurface formation.

In another aspect, the system may include a plurality of additional thermal sensors, each of the plurality of additional thermal sensors in communication with the data logger and to obtain at least one temperature at a corresponding subsurface location. The system may also include a vertical structure supporting the first thermal sensor, second thermal sensor, and the plurality of additional thermal sensors in a vertical arrangement in the subsurface formation.

Another aspect of the present disclosure may include the executable instructions further configured to calculate, utilizing the least one obtained temperature at the first subsurface location, the least one obtained temperature at the second subsurface location, and the estimated planar location of the subsurface heating or cooling source, an expected temperature distribution within the subsurface formation and obtain a set of obtained temperatures from the plurality of additional thermal sensors; and correlate each of the set of obtained temperatures to a corresponding subsurface location. The instructions may also be configured to compare the set of obtained temperatures to the expected temperature distribution within the subsurface formation and generate, based on the comparison, a comparison value comprising a calculated difference between the set of obtained temperatures and the expected temperature distribution. In response to the comparison value exceeding an allowable tolerance value, the computing device may adjust the estimated planar location of the subsurface heating or cooling source.

Yet another aspect of the present disclosure may include the system including a display device and the executable instruction displaying on the display device a visual representation of the rate of change of the amount of the organic material. The visual representation of the rate of change of the amount of the organic material may include a rate of change of the amount of the organic material over a period of time.

Through the systems and methods described herein, NSZD rates for a subsurface region may be determined or estimated and a remedial action, such as a clean-up schedule to remove LNAPLs from the subsurface region, may be established. The method provided may therefore be based on rigorous first principle of heat flow while eliminating a potentially problematic need to collect background temperature data, including removal of errors associated with non-representative background measurements or corrections and the need for additional background data-gathering materials or components.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

The application file contains at least one photograph executed in color. Copies of this patent application publication with color photographs will be provided by the Office upon request and payment of the necessary fee.

The following figures illustrate various aspects of the disclosure.

Corresponding reference characters indicate corresponding elements among the views of the drawings. The headings used in the figures should not be interpreted to limit the scope of the claims.

DETAILED DESCRIPTION

Figure 1A:
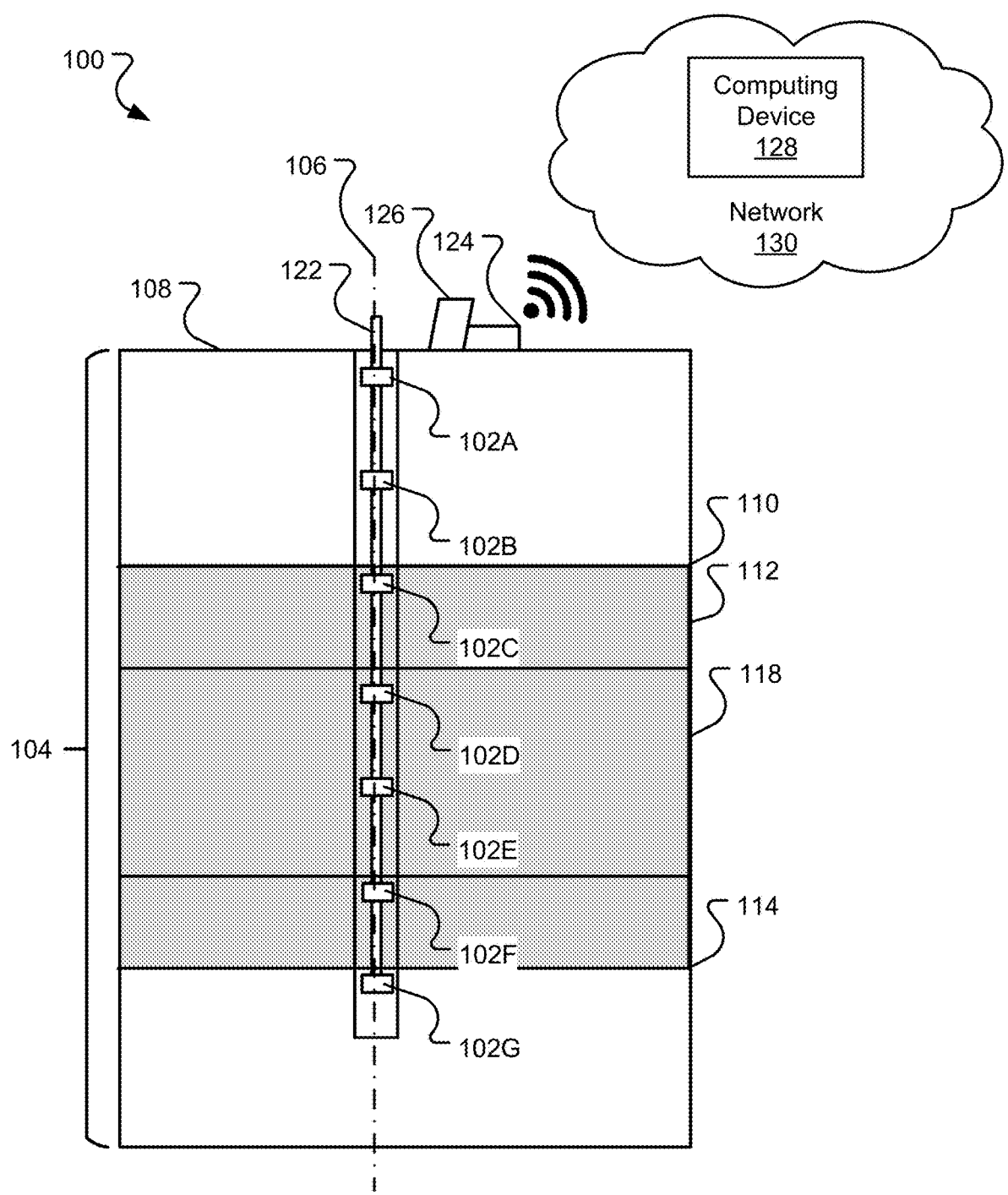
FIG. 1A is a schematic representation of a subsurface thermal monitoring system installed within a subsurface formation.

In various aspects, the present disclosure provides systems and methods for measuring a rate of change in an amount of a reactive material within a subsurface formation using measurements of thermal parameters at one or more positions within the formation. These systems and methods may measure thermal parameters including, but not limited to, thermal gradients and/or temperatures at one or more positions within the subsurface formation. The measured thermal parameters may be used to determine the heat generated by the degradation of the reactive material. The method may then convert the heat generated by the degradation of the reactive material to a rate of change in the amount of reactive material within the subsurface formation using the known change in enthalpy for the degradation reactions known to break down the reactive materials within the subsurface formation.

Previously, methods and systems to measure a rate of change in the amount of reactive material within a subsurface formation required correction of thermal parameters measured by removing the effects of other thermal sources and sinks within the subsurface formation, such as geothermal heat sources, solar radiation at ground level, daily variations in air temperature at ground level, and seasonal variations in air temperature at ground level. However, such corrections to the thermal parameters to account for background thermal parameters may result in erroneous natural source zone depletion (NSZD) calculations, particularly in areas in which light non-aqueous phase liquids (LNAPLs) are not present and/or present under asphalt.

The systems and methods described herein therefore overcome many of the limitations of existing methods of monitoring the rate of degradation of a reactive material within a subsurface formation. In particular, the systems and methods provide for real-time monitoring of subsurface temperature profiles to resolve NSZD rates for shallow petroleum liquids by transforming temperature data into NSZD rates. In one instance, a first temperature measurement may be obtained near the surface of a subsurface region and a second temperature measurement may be obtained further from the surface of the subsurface region.

Thermal parameters associated with surface heating/cooling and a subsurface heating/cooling source may be determined from two derived heat flow equations. In some instances, an estimated location of a planar subsurface heat source/sink due to exothermic degradation reactions within the subsurface may be selected. Such exothermic reactions may be a result of heat-generating biodegradation of organic reactive materials such as hydrocarbons, oxidation of inorganic reactive materials including metals, and radioactive decay of radioactive materials. With the derived thermal parameters and the estimated location of the subsurface heat source/sink, NSZD rates for the subsurface region may be determined or estimated and a remedial action, such as a clean-up schedule to remove LNAPLs from the subsurface region, may be established. The method provided may therefore be based on rigorous first principle of heat flow while eliminating a potentially problematic need to collect background temperature data.

In one aspect, an iterative process may be executed to determine the estimated location of the subsurface heating/cooling source. The iterative process may include calculating a temperature distribution through the subsurface region based on an initial estimated location of the subsurface heating/cooling source and the thermal parameters associated with surface heating/cooling and a subsurface heating/cooling source discussed above. The calculated temperature distribution may be compared to a set of collected or obtained temperature measurements within the subsurface region and a difference between the estimated temperature distribution and the measured temperature distribution may be determined. The difference between the temperature distributions may be analyzed or compared to an allowable tolerance and, in instances where the difference between the distributions exceeds the allowable tolerance, a new estimated location of the subsurface heating/cooling source may be selected. This process may continue until a location for the subsurface heating/cooling source is selected that provides an estimated temperature distribution within the subsurface region that is within an allowable tolerance of a measured temperature distribution. This iterative process may ensure the estimated location of the subsurface heating/cooling source is accurate.

In one aspect, the measured thermal parameters may capture the effect of exothermic degradation reactions including, but not limited to: heat-generating biodegradation of organic reactive materials such as hydrocarbons, oxidation of inorganic reactive materials including metals, and radioactive decay of radioactive materials. In another aspect, the measured thermal parameters may capture the effect of endothermic reactions including, but not limited to, the evaporation of volatile reactive materials within the subsurface formation. In various aspects, the systems and methods disclosed herein may monitor the rate of change of the amount of any reactive materials which undergoes any reaction within the subsurface formation that results in any change in temperature including but not limited to heat-generating exothermic reactions and heat-absorbing endothermic reactions.

In various other aspects, a thermal monitoring system may be used to obtain the measurements of thermal parameters for at least one position within the subsurface formation. In various aspects, the thermal monitoring system may enable a one-dimensional, two-dimensional, or three-dimensional energy balance for the reactive material subsurface formation. In one aspect, the measurements of the thermal parameters may be obtained along a linear transect, resulting in a one-dimensional characterization of the thermal parameters within the reactive material subsurface formation. By way of non-limiting example, thermal parameters may be measured along a vertical transect to provide a characterization of the thermal parameters as a function of depth below ground surface of the formation (or the top surface of the formation, if the surface extends above ground, e.g., as with a landfill or composting site). In another aspect, the measurements of the thermal parameters may be obtained within a planar array, resulting in a two-dimensional characterization of the thermal parameters within the reactive material subsurface formation. By way of non-limiting example, thermal parameters may be measured along two vertical transects separated laterally, thereby providing a characterization of the thermal properties as a function of depth below ground or top surface of the formation and as a function of the horizontal distance in the plane defined by the two vertical transects. By way of yet another non-limiting example, thermal parameters may be measured along three non-coplanar transects, thereby providing a three-dimensional characterization of the thermal properties within the reactive material subsurface formation.

Conductive heat flow may be assessed using temperature gradients measured within the region of the subsurface formation adjacent to the region including the reactive material as described herein below. In various aspects, the temperature gradients may be measured in any one or more directions including, but not limited to: vertical; horizontal including left/right and/or north/south/east/west; and any combination thereof. In one aspect, the temperature gradient may be measured directly using a temperature gradient sensor as described herein below. In another aspect, the temperature gradient may be assessed by obtaining temperature measurements at two or more positions along a desired direction. By way of non-limiting example, two temperature sensors positioned at two positions along a vertical transect may be positions within the region of the subsurface formation situated vertically above a region including the reactive material to measure the temperature gradient above the region including the reactive material.

Additional descriptions of the systems and methods for monitoring the rate of change of an amount of a reactive material within a subsurface formation are provided herein below.

The method of the present disclosure in various aspects may be used to monitor changes in the amount of a reactive material within a subsurface formation using measured thermal parameters including, but not limited to, thermal gradient and temperature within the subsurface formation. "Subsurface formation", as used herein, refers to any local region including a ground or top surface area and a volume of substrate situated vertically beneath the exposed ground or top surface. In various aspects, the subsurface formation may include a substrate or porous media including, but not limited to, soil, sand, clay, porous rock, non-porous rock, man-made substrates such as asphalt or concrete, and any combination thereof. In various other aspects, the substrate of subsurface formation may further include water at various saturation levels ranging from relatively dry substrate to completely saturated substrate including, but not limited to groundwater. The subsurface formation may further include various organisms including, but not limited to, bacteria, fungi, plant roots, and burrows of larger organisms including, but not limited to: insect larvae, adult insects such as ants, amphibians such as frogs or salamanders, reptiles such as snakes or lizards, and mammals such as mice, rabbits, or moles.

Figure 1B:
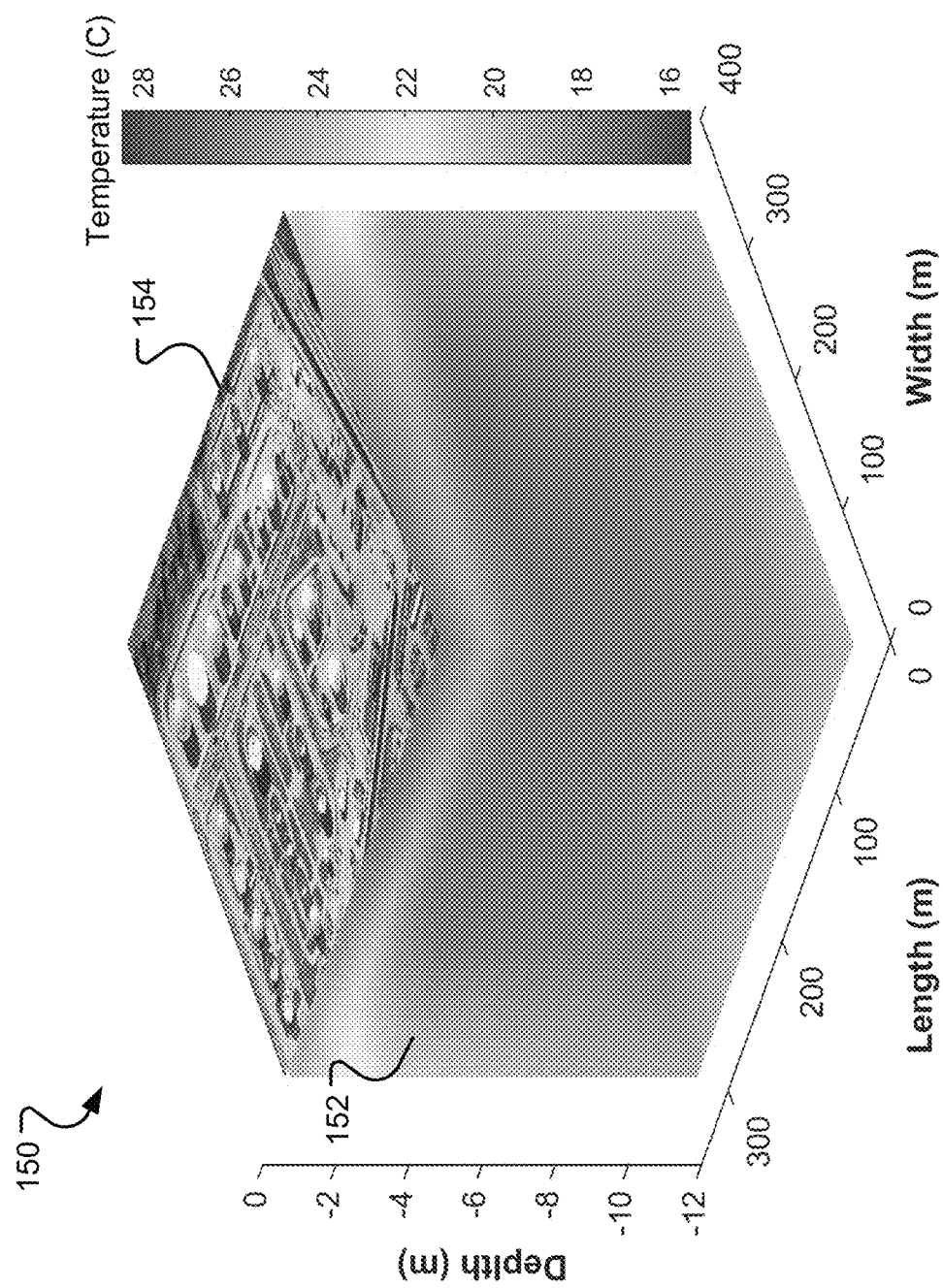
FIG. 1B is a three-dimensional representation of measures of subsurface temperatures at a fuel terminal site.

In one aspect, the subsurface thermal monitoring system may be used to monitor the at least one thermal parameter at one or more positions within the subsurface formation. FIG. 1A is a schematic representation of a subsurface thermal monitoring system 100 installed within a subsurface formation in one aspect and FIG. 1B is a three-dimensional representation of measures of subsurface temperatures at a fuel terminal site. The system 100 may include a plurality of temperature sensors 102 including, but not limited to, temperature sensors 102A, 102B, 102C, 102D, 102E, 102F, and 102G as illustrated in FIG. 1A. In various aspects, plurality of temperature sensors 102 may be situated at any position relative to one another within the subsurface formation 104 without limitation. In various aspects, the plurality of temperature sensors 102 may be arranged to monitor one or more temperature gradients in one dimension, such as vertically as illustrated in FIG. 1A, in two dimensions, and/or in three dimensions, such the systems described in related U.S. patent application Ser. No. 16/600,946 titled "Devices and Methods for Measuring Temperature, Oxidation Reduction Potential, and Water-Level Within a Subsurface Formation" to Sale et al., the entire contents of which are hereby incorporated fully by reference. FIG. 1B illustrates an example temperature gradient 150 of a subsurface formation 152 that may be present at a site 154 due to various heat sources, including surface heating and/or subsurface heating.

As described herein, the temperature sensors 102A, 102B, 102C, 102D. 102E. 102F, and 102G may be situated along a vertical transect 106 extending mostly vertically downward from the ground or surface level 108. In one aspect, the temperature sensors 102 may extend to a distance below the upper extent 110 of the reactive materials 112 to below the lower extent 114 of the reactive materials 112. In another aspect, the temperature sensors 102 may extend to a distance below the upper extent 110 of the reactive materials 112 to below a water table fluctuation area 118 within the subsurface formation 104.

Any known suitable temperature sensor may be used in the system 100 without limitation including, but not limited to: thermocouples, thermistors, resistance temperature detectors, silicon bandgap temperature detectors, and any other suitable temperature sensor known in the art. In another aspect, the system 100 may include one or more thermal gradient sensors (not shown) including, but not limited to, a thermal gradient plate such as a Peltier cooler. In this other aspect, the one or more thermal gradient sensors may be situated above the upper extent 110 and/or below the lower extent 114 of the reactive materials 112.

The device 100 may further include one or more additional sensors to measure additional data that may be used to determine thermal fluxes within the subsurface formation 104. In one aspect, a water level sensor (not shown) may be included in the system 100 to monitor the vertical movement of the water levels within the subsurface formation 104 to help determine vertical convective energy flux due to vertical water movement as described herein above.

In other aspects, the system 100 may further include a support 122 to which the temperature sensors 102 and/or additional sensors may be attached and maintained in a desired vertical position relative to ground level 108 of the subsurface formation 104. In various aspects, the support may be an elongate, stiff member that may be introduced into a monitor well or other channel reaching down a suitable distance into the subsurface formation. In addition, the support 122 may be sufficiently flexible to be wound on a spool for transport and delivery at a monitor site. In another aspect, the diameter of the support may be sufficiently small to ensure compatibility with existing deep drilling systems. In one aspect, the support may be a formed from PVC tubing with an outer diameter of about ⅜".

In another aspect, the system 100 my further include a data logger 124 operatively coupled to the temperature sensors 102 and/or additional sensors. In this aspect, the data logger 124 may receive and store a plurality of readings from the temperature sensors 102 and/or additional sensors over a period of time and may additionally transmit or download the stored data via any one or more known means including, but not limited to direct downloading of the stored data to a storage device such as a jump drive, portable hard drive, or other suitable storage device, transmittal of the data via telephone lines, over an Internet network, over a wireless data network, or via any other known data communication means. One example of a control system for logging the received temperatures is illustrated in related U.S. patent application Ser. No. 16/600,946. In yet another aspect, the system 100 may further include a data transmittal device including, but not limited to a radio transmitter (not shown) and/or a digital cellular modem operatively connected to the data logger 124. Any known suitable data transmittal device may be incorporated into the system 100 without limitation.

In another additional aspect, the system 100 may further include a power source 126 operatively connected to the temperature sensors 102 and/or additional sensors and the data logger 124. Any known power source 126 may be used in the system 100 without limitation including, but not limited to a solar panel, a battery, a power line, and any other suitable power source.

In one particular example, the system 100 may include a vertical string of type-T copper-constant thermocouples 102. Thermocouples 102 may be fabricated using PFA-coated thermocouple wire spot-welded together at the end of the wire, with the spot welds enclosed in epoxy-filled glass caps. The thermocouples 102 may be attached to 9.5 mm OD PVC rods 122 to control the depth of installation. Each thermocouple 102 may be connected to a data logger 126 powered by a 12-V DC, 24 amp-h sealed rechargeable battery, which may be charged by a 20-W solar panel. A 12-V charge regulator may regulate the current between the solar panel, battery, and data logger. A cellular digital modem connected to the data logger 124 may transmit via a cellular network 130 and the data logger, battery, charge regulator, and cellular digital modem may be housed inside a protective, weather-resistant enclosure. Recorded subsurface temperatures by the data logger 124 may be sent daily to a computer 128 over the cellular network 130.

Through the system 100 of FIG. 1, various thermal parameters of the subsurface area 104 may be obtained via the one or more temperature sensors 102. Methods have been proposed to utilize such thermal parameters to determine NSZD rates within an area with LNAPL. However, such methods have typically required an adjustment to measured thermal parameters for background correction for surface heating and cooling, resulting in both unreliable determined NSZD rates (due to the inability to locate a background location similar to an LNAPL-impacted location) and added equipment to obtain the background thermal parameters. An alternate method for monitoring a rate of change in an amount of reactive material within a subsurface formation is presented herein and illustrated in FIG. 2. In particular, the method provided removes a necessity for conducting a correction of the thermal parameters for background thermal effects, thereby improving the accuracy of the characterization of the rate of change of energy within a region including the reactive material of the subsurface formation while reducing the equipment or readings used for the characterization. In one aspect, the rate of change of energy within the region including the reactive material may be converted to a rate of change of the amount of reactive material within the subsurface formation to determine contaminants in the subsurface region.

Figure 2:
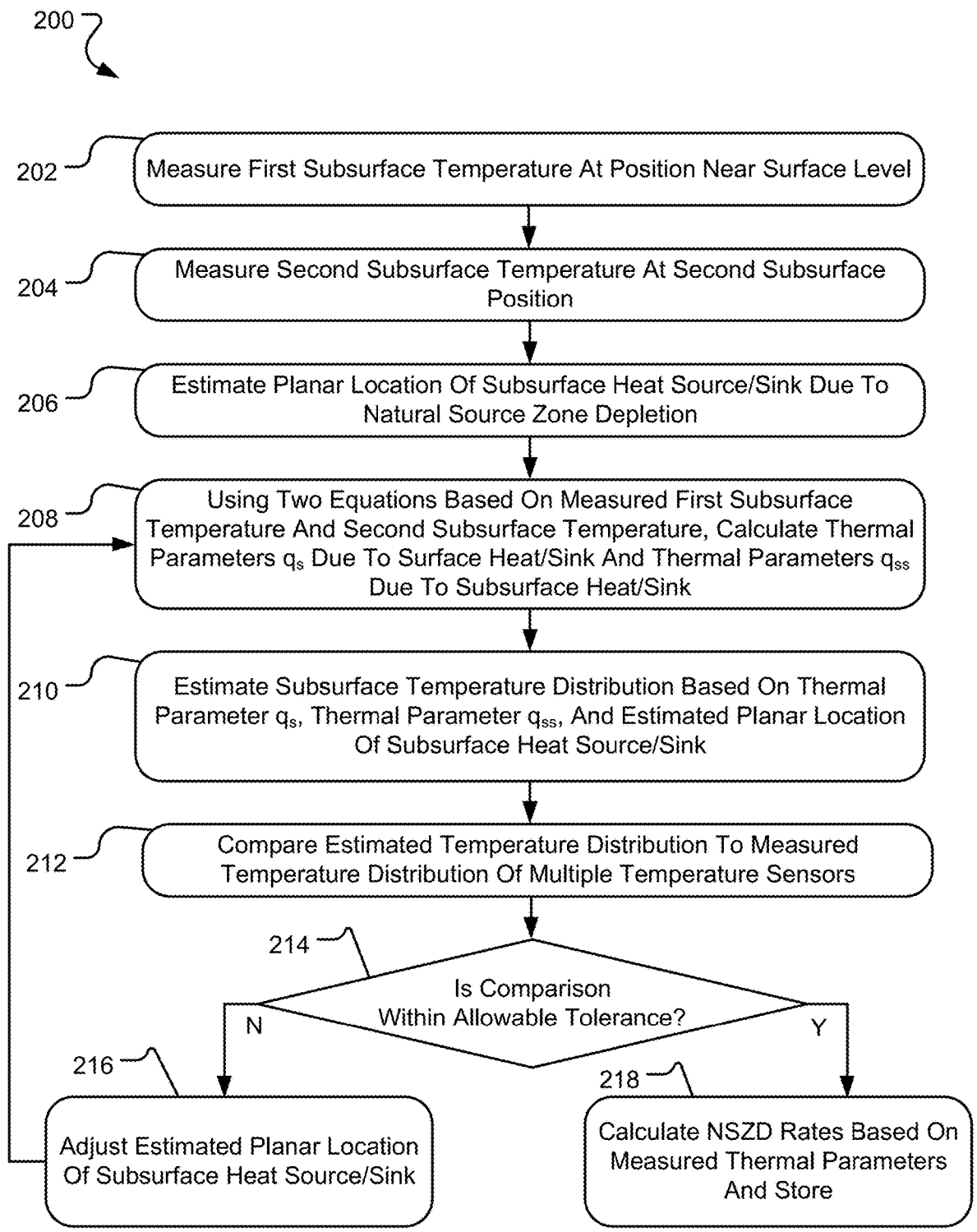
FIG. 2 is a flowchart of a method for monitoring a rate of change in an amount of reactive material within a subsurface formation without background correction.

Referring to FIG. 2, the method 200 includes obtaining measurements of at least one thermal parameter for at least one position within the subsurface formation at step 202 without background correction. In various aspects, the thermal parameters may include parameters to be used in the energy balance, such as temperature or a measured rate of change of temperature over time. In some instances, the steps of the method 200 may be performed by a computing device 128 associated with the data logger 124 or otherwise in communication with the sensor array 122. For example, the data logger 124 itself may include computing components to perform one or more of the steps below. In another example, a computing device 128, such as a laptop computer, cloud computing environment, mobile computing device, and the like, may be in communication with the data logger 124 to receive data and perform one or more of the steps of the method 200 on the received data, perhaps via a network 130. In some instances, the steps of the method 200 may be performed by more than one component. For example, a temperature sensor 102 may perform some steps, the data logger 124 may perform other steps, and a computing device may perform still other steps of the method 200. The steps may be executed through one or more hardware components, software programs, or a combination of both hardware and software components.

In one aspect, the method 200 may measure temperature within the region including the reactive material over a predetermined time interval at step 202, and the time history of the measured temperature may be processed using known methods to calculate the rate of change in temperature. The temperature measurement may be performed using any suitable temperature sensor described in detail herein below. In general, the location within the subsurface at which the first thermal parameter is obtained may be near the surface level 108 of the subsurface region 104. For example, temperature sensor 102A may obtain the thermal parameter measurement as the sensor nearest the surface level 108 of the string of sensors. However, the choice of the position within the subsurface formation at which to perform measurements can and will vary depending on any one or more of a variety of factors including, but not limited to: available instrumentation, accessibility of formation to thermal sensors, unique characteristics of the formation, and any other relevant factor.

At step 204, a second subsurface thermal parameter may be measured at a second subsurface position, typically below the position of the first thermal parameter. For example, a second thermal parameter may be obtained from sensor 102B, 102C, 102D, 102E, 102F, or 102G, although the position within the subsurface formation 104 at which to perform the second measurement can and will vary. In some instances, the position of the first and second thermal parameters may be determined in relation to the other sensors 102 along the sensor system 100. For example, sensor 102A may be provide the measured thermal parameter to data logger 124 with an indicator of sensor 102A. The other sensors 102 along the array 122 of sensors may similarly provide the measured thermal parameters with an indication of the sensor from which the parameter is sent. In this manner, the data logger 124 and other devices receiving the measured thermal parameters may determine the sensor providing the parameter and the position of the measuring sensor within the array of sensors 102. Although discussed in relation FIG. 2 as measuring thermal parameters at two locations, it should be appreciated that any number of thermal parameters may be measured by the sensor array 122 at any position along the array such that more than two such measurements may be obtained.

Figure 3:
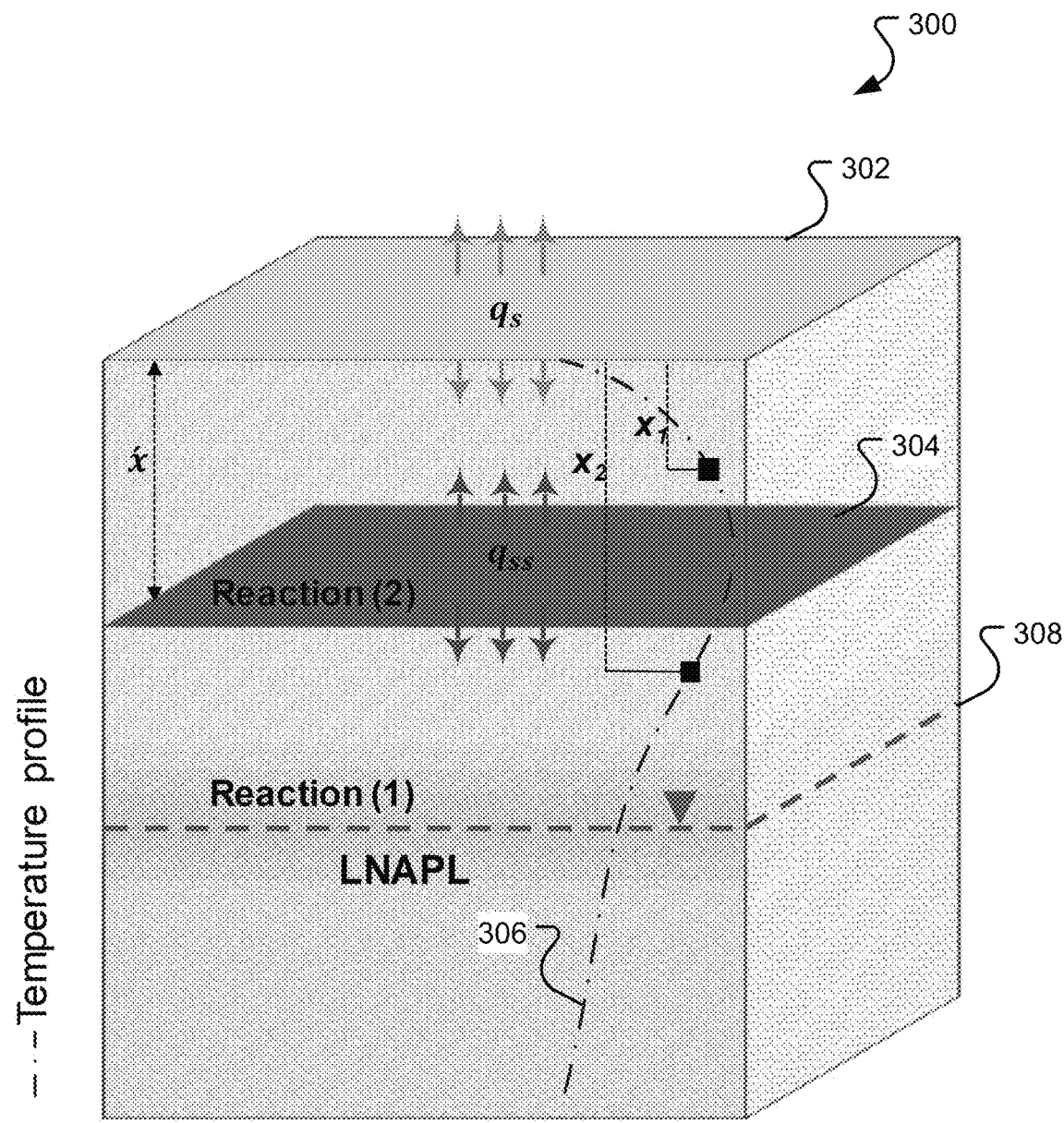
FIG. 3 is a schematic representation of a model of heat sources within a light non-aqueous phase liquids-impacted area.

As mentioned above, the thermal parameters obtained from the sensors 102 of the system 100 may be utilized to determine NSZD rate as a function of the measured temperatures along the sensor array 122. In particular, a governing equation for conductive heat transfer is:

$$\frac{\partial}{\partial x}\left(K_x \frac{\partial T}{\partial x}\right) + \frac{\partial}{\partial y}\left(K_y \frac{\partial T}{\partial y}\right) + \frac{\partial}{\partial z}\left(K_z \frac{\partial T}{\partial z}\right) = \frac{\partial C\rho T}{\partial t} \quad (1)$$

where K (M/T³θ) is thermal conductivity, C (L²/T²θ) is heat capacity, T is temperature (θ), t (T) is time, ρ (M/L³) is sediment density, and (x, y, z) (L) are spatial coordinates. FIG. 3 shows a conceptual model 300 of the primary heat sources in a LNAPL-impacted area. In particular, the model 300 illustrates a subsurface region, similar to the subsurface region 104 of FIG. 1. As discussed, the surface level (represented as plane 302) provides a heat source/sink $q_s$ (measured in M/T³) into the subsurface region. At some depth x, a second subsurface heat source/sink $q_{ss}$ (measured in M/T³) occurs due to the exothermic degradation reactions within the subsurface including, but not limited to: heat-generating biodegradation of organic reactive materials such as hydrocarbons, oxidation of inorganic reactive materials including metals, and radioactive decay of radioactive materials. In one example, a first reaction may occur at depth 308 mediated by methanogens under anaerobic conditions producing $CH_4$ and $CO_2$. Methanogenesis typically occurs in and about the space where LNAPLs are present. In the second reaction occurring at depth 304, methanotrophs aerobically oxidize methane into $CO_2$ and $H_2O$. Oxidation of $CH_4$ occurs above the LNAPL body at a vertical position where the outward flux of $CH_4$ meets an inward flux of atmospheric $O_2$. Notably, the inward flux of oxygen can vary with time due to temporally varying effective oxygen diffusion coefficient (controlled by soil water content), barometric pumping, and water table fluctuations. In general, this second reaction 304, oxidation of methane, provides the primary source of heat for NSZD.

As such, subsurface heat source/sink $q_{ss}$ 304 associated with this second reaction occurs at a temporally varying position, x=x̄ in relation to the surface level 302 (at x=0.) At any point in the domain, temperature may a function of the temporal values of $q_s$, $q_{ss}$, and x̄, as illustrated by line 306 illustrating the temperature at each depth x.

Initially, the depth x̄ may not be known as the depth varies temporally. Thus, in step 206, an estimated planar location of x̄ may be selected for the heat source/sink associated with the NSZD depletion. The estimated planar location of the subsurface heat source/sink 304 may be any depth in relation to surface level 302. In one example, the planar location x̄ of the subsurface heat source/sink 304 may be estimated at a midpoint between the upper extant 118 of the water table 116 of the subsurface region 104 and the surface level 108, although any location within the subsurface region may be chosen.

At step 208, the thermal parameters $q_s$, $q_{ss}$ may be determined utilizing the measured first subsurface temperature, the measured second subsurface temperature, and the estimated planar location of the subsurface heat source/sink 304 as inputs for equation (1). In particular, applying assumptions of model 300 of FIG. 3, equation (1) may be reduced to:

$$\frac{\partial^2 T}{\partial x^2} = \frac{1}{\kappa}\frac{\partial T}{\partial x} \qquad (2)$$

Such assumptions may include the surface heat source/sink 302 and subsurface heat sources/sink 304 can be approximated as planar features, thermal properties of soil are independent of position, direction, temperature, and time, horizontal heat fluxes are negligible, temporally varying surface and subsurface heat source/sink can be approximated using a succession of steady-state (e.g., daily) values, the surface heating and cooling term addresses the processes controlling surface heating and cooling including, but not limited to, solar radiation, black body radiation, incident precipitations, evaporative cooling, and composting shallow soil organic compounds, The subsurface heat source/sink has a temporally varying position $\dot{x}$ (approximated using a succession of steady-state values) and an image source/sink symmetrically located at position $-\dot{x}$, net gain or of loss of biomass, precipitation, or dissolution of minerals, or changes in thermodynamic states do not contribute significantly to subsurface heating and cooling, geothermal temperature gradients are negligible, observed nearly-constant temperatures at depth are the basis for initial condition temperature conditions, and the energy produced from mineralization of decane is representative of the energy produced through NSZD of the hydrocarbons of concern.

Given the stated assumptions, boundary and initial conditions may include:

$$q_s = -K\frac{dT}{dx}\Big|_{x=0} \qquad (3)$$

$$T(\pm\infty, t) = T_0 \qquad (4)$$

$$T(x, 0) = T_0 \qquad (5)$$

where $T_0$ is initial temperature, and $\kappa = K/\rho c$ is thermal diffusivity ($L^2/T$). A solution for Equation (2) may be obtained by superimposing separate solutions for temperatures associated with $q_s$ and $q_{ss}$. For example, a solution for temperature as a function of $q_s$ is:

$$T(x, t) - T_0 = \frac{2q_s}{K}\left\{\sqrt{\frac{\kappa t}{\pi}}\exp\left(-\frac{x}{4\kappa t}\right) - \frac{x}{2}\mathrm{erfc}\left(\frac{x}{\sqrt{4\kappa t}}\right)\right\} \qquad (6)$$

which satisfies all conditions of Equations (3), (4), and (5).

A solution for temperature as a function of $q_{ss}$ at $\dot{x}$ is:

$$T(x, t) = \frac{q_{ss}}{\rho c}\left\{\sqrt{\frac{t}{\pi\kappa}}\exp\left(-\frac{(x-\dot{x})^2}{4kt}\right) - \frac{|x-\dot{x}|}{2k}\mathrm{erfc}\left(\frac{|x-\dot{x}|}{\sqrt{4kt}}\right)\right\} + \frac{q_{ss}}{\rho c}\left\{\sqrt{\frac{t}{\pi\kappa}}\exp\left(-\frac{(x+\dot{x})^2}{4kt}\right) - \frac{(x+\dot{x})^2}{2k}\mathrm{erfc}\left(\frac{(x+\dot{x})}{\sqrt{4kt}}\right)\right\} \qquad (7)$$

The first term in Equation (7) accounts for the real subsurface NSZD heat source. The second term in Equation (7) is an imaginary source located in imaginary space, at a position equidistant to the real subsurface heat source above the ground surface. Summation of Equation (6) and Equation (7) yields:

$$T(x, t) - T_0 = \frac{2q_s}{K}\left\{\sqrt{\frac{\kappa t}{\pi}}\exp\left(-\frac{x}{4\kappa t}\right) - \frac{x}{2}\mathrm{erfc}\left(\frac{x}{\sqrt{4\kappa t}}\right)\right\} + \qquad (8)$$

$$\frac{q_{ss}}{\rho c}\left\{\sqrt{\frac{t}{\pi\kappa}}\exp\left(-\frac{(x-\dot{x})^2}{4kt}\right) - \frac{|x-\dot{x}|}{2k}\mathrm{erfc}\left(\frac{|x-\dot{x}|}{\sqrt{4kt}}\right)\right\} +$$

$$\frac{q_{ss}}{\rho c}\left\{\sqrt{\frac{t}{\pi\kappa}}\exp\left(-\frac{(x+\dot{x})^2}{4kt}\right) - \frac{(x+\dot{x})}{2k}\mathrm{erfc}\left(\frac{(x+\dot{x})}{\sqrt{4kt}}\right)\right\}$$

In net, the combination of real surface and subsurface heat sources and an imaginary subsurface heat source leads to a mathematical framework where NSZD heat can leave the real model domain at x=0.

A solution accounting for temporal variations in $q_s$, $q_{ss}$, and $\dot{x}$ is obtained using a succession of steady states:

$$T(x, t) - T_0 = \sum_{i=1}^{n}\left(q_s^i - q_s^{i-1}\right)F(x, t - t_{i-1}) + \left(q_{ss}^i - q_{ss}^{i-1}\right)G\left(x, t - t_{i-1}, \dot{x}\right) \qquad (9)$$

where $q_s$, $q_{ss}$, and $\dot{x}$ are assumed constant between consecutive time steps ($t_{n-1} < t \leq t_n$) and:

$$F(x, t - t_{i-1}) = \qquad (10)$$

$$\frac{2}{K}\left\{\sqrt{\frac{\kappa(t - t_{i-1})}{\pi}}\exp\left(-\frac{x}{4\kappa(t - t_{i-1})}\right) - \frac{x}{2}\mathrm{erfc}\left(\frac{x}{\sqrt{4\kappa(t - t_{i-1})}}\right)\right\}$$

$$G(x, t - t_{i-1}, \dot{x}) = \qquad (11)$$

$$\frac{1}{\rho c}\left\{\sqrt{\frac{(t - t_{i-1})}{\pi\kappa}}\exp\left(-\frac{(x-\dot{x})^2}{4\kappa(t - t_{i-1})}\right) - \frac{|x-\dot{x}|}{2k}\mathrm{erfc}\left(\frac{|x-\dot{x}|}{\sqrt{4\kappa(t - t_{i-1})}}\right)\right\} +$$

$$\frac{1}{\rho c}\left\{\sqrt{\frac{(t - t_{i-1})}{\pi\kappa}}\exp\left(-\frac{(x-\dot{x})^2}{4\kappa(t - t_{i-1})}\right) - \frac{(x-\dot{x})}{2k}\mathrm{erfc}\left(\frac{(x-\dot{x})}{\sqrt{4\kappa(t - t_{i-1})}}\right)\right\}$$

By measuring temperature in the subsurface at two different positions, Equation (9) can be solved in the following two-equation two-unknown system for determining the values of $q_s$ and $q_{ss}$:

$$\begin{cases} T(x_1, t) = \sum_{i=1}^{n}\left(q_s^i - q_s^{i-1}\right)F(x, t - t_{i-1}) + \left(q_{ss}^i - q_{ss}^{i-1}\right)G(x, t - t_{i-1}, \dot{x}) \\ T(x_2, t) = \sum_{i=1}^{n}\left(q_s^i - q_s^{i-1}\right)F(x, t - t_{i-1}) + \left(q_{ss}^i - q_{ss}^{i-1}\right)G(x, t - t_{i-1}, \dot{x}) \end{cases} \qquad (12)$$

As such, the two equations illustrated in Equation (12) may be solved to obtain for $q_s$ and $q_{ss}$ for model 300 in step 208. However, as expressed in Equation (8), except for $q_s$ and $q_{ss}$, $\dot{x}$ is unknown. Therefore, the two equations may be solved utilizing the estimated planar location $\dot{x}$ determined above to obtain $q_s$ and $q_{ss}$ for model 300. In particular and using Equation (9) above, an estimated subsurface temperature distribution ($T_{Prd}$) may be determined based on the on thermal parameter $q_s$, thermal parameter $q_{ss}$, and the estimated planar location of subsurface heat source/sink 304 in step 210. The estimated subsurface temperature distribution provides an estimated temperature at any location x́ below surface level 302 for circumstances where the subsurface location 304 is at the estimated planar location discussed above. With the estimated temperature distribution, a comparison to observed temperature distribution may be performed in step 212. More particularly, multiple temperature measurements may be obtained from the sensor array 122 in addition to the first temperature measurement taken at sensor 102A and the second temperature measurement taken at a lower sensor, such as sensor 102F. Additional temperature measurements may be obtained by sensor 102B, 102C, 102D, 102E, and/or 102G. The collection or set of temperature measurements obtained by the sensors 102 of the sensor array 122 may be compared to the estimated temperature distribution determined above based on the location of the corresponding sensor. For example, an estimated temperature at the location of sensor 102C determined from the Equations above and based on the estimated location of the subsurface heat source/sink 304 may be compared to an obtained temperature measurement by sensor 102C. A similar comparison may be made for each obtained subsurface temperature measurement corresponding to a relative location of the sensor from which the obtained measurement is received.

In some instances, the comparison of the estimated temperature distribution ($T_{Prd}$) and the observed temperature distribution ($T_{Obs}$) may result in a comparison value or quantifiable difference. In one particular instance, a root mean squared error (RMSE) and coefficient of determination ($R^2$) may be obtained from the comparison, although any method for determining a difference of a comparison of sets of values may be utilized. In step 214, the result of the comparison of the estimated temperature distribution ($T_{Prd}$) and the observed temperature distribution ($T_{Obs}$) may be compared to an allowable tolerance value. If the comparison value exceeds the allowable tolerance, an adjusted planar location for the subsurface heat source/sink 308 may be selected at step 216. For example, the estimated planar location of the subsurface heat source/sink 308 may be selected one meter above the previous estimated location, although any distance from the previous estimated location may be selected. In another example, the estimated planar location of the subsurface heat source/sink 308 may be selected below the previous estimated location. In still further examples, the estimated planar location of the subsurface heat source/sink 308 may alternate between being adjusted above the previous estimated location and below the previous estimated location. Upon adjusting the estimated planar location of the subsurface heat source/sink 308, the method 200 may return to step 208 to recalculate $q_s$ and $q_{ss}$ at the adjusted x́.

Through the above steps, the estimated planar location of the subsurface heat source/sink 308 may be adjusted until the comparison of the estimated temperature distribution ($T_{Prd}$) and the observed temperature distribution ($T_{Obs}$) is within an acceptable tolerance. In other words, the estimated planar location of the subsurface heat source/sink 308 may be adjusted until the effects of the subsurface heat source/sink 308 at each location along the sensor array 122 is estimated within an allowable tolerance. In this manner, the position of the subsurface heat source/sink 308 may be iteratively adjusted to an allowable location within the subsurface region.

Once the iterative adjustment to the estimated planar location of the subsurface heat source/sink 308 is within the allowable tolerance, the values of subsurface heat source ($q_{ss}$) are converted to NSZD rates, on a volumetric basis. In one particular example, the values of subsurface heat source ($q_{ss}$) may be converted to NSZD rates using:

$$N\dot{S}ZD = \frac{-q_{ss}}{\Delta H_{decane} \rho_{decane}} \quad (13)$$

where $N\dot{S}ZD$ is the rate of NSZD (L/T), $\Delta H_{decane}$ is the enthalpy of complete mineralization ($ML^2/T^2$/mol), and $\rho_{decane}$ is the molar density of decane=5.14 (mol/L). In various other aspects, additional measurements of other characteristics of the subsurface formation may be obtained for use in determining NSZD rates of an area. Non-limiting examples of suitable additional measurements include: ground water level; % water saturation at one or more positions; water flow rate; thermal conductance of the substrate within the subsurface formation, heat capacity of the substrate within the subsurface formation, and any other suitable characteristics of the subsurface formation used in the energy balance calculations as described herein below.

Figure 4:
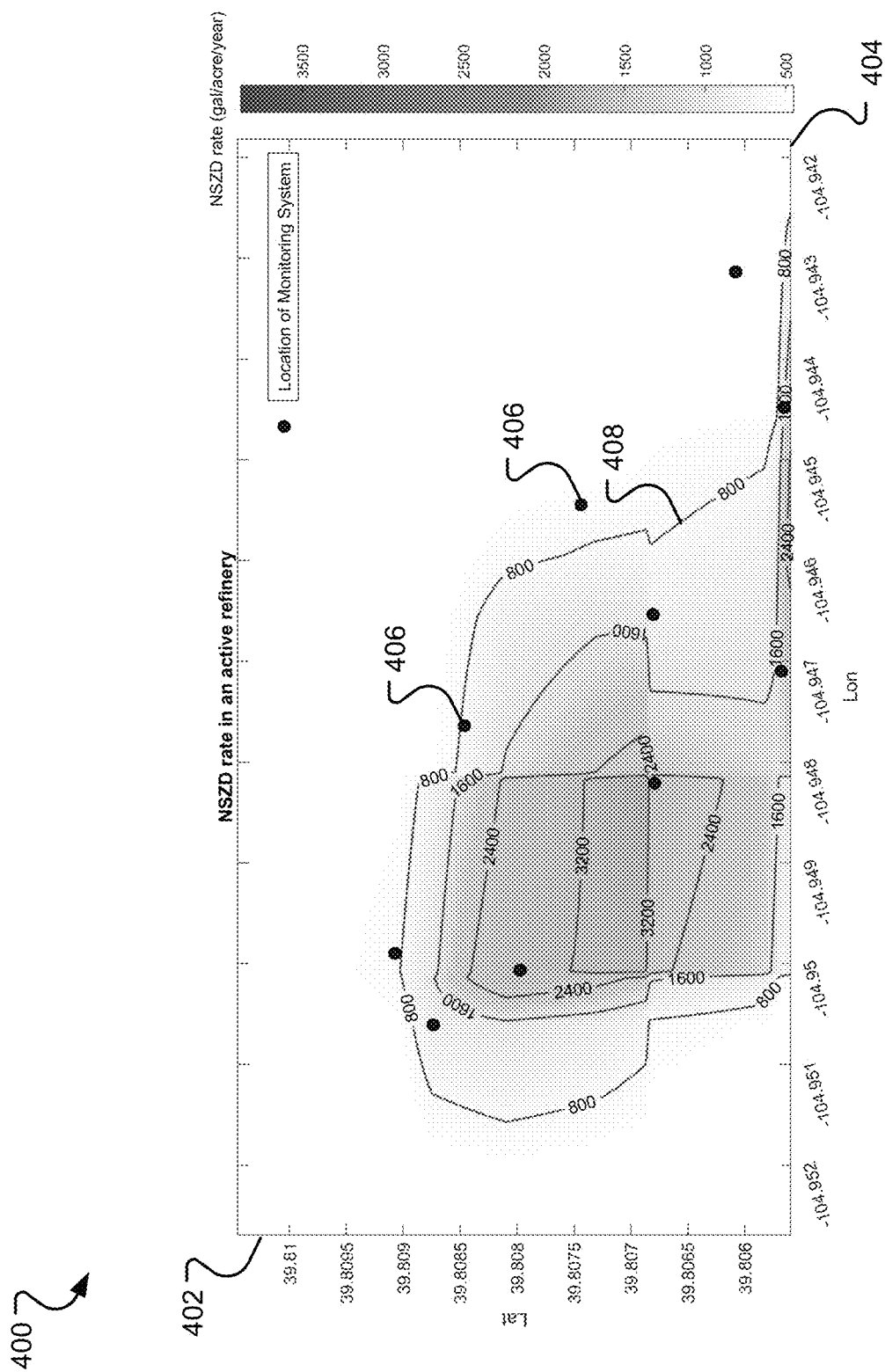
FIG. 4 is a graph of measured and estimated natural source zone depletion rate in a light non-aqueous phase liquids-impacted area determined from the method of FIG. 2.

The obtained NSZD rates may be utilized to understand the effect of exothermic degradation reactions including, but not limited to: heat-generating biodegradation of organic reactive materials such as hydrocarbons, oxidation of inorganic reactive materials including metals, and radioactive decay of radioactive materials. In another aspect, the measured thermal parameters may capture the effect of endothermic reactions including, but not limited to, the evaporation of volatile reactive materials within the subsurface formation. By monitoring the rate of change of the amount of reactive materials which undergoes a reaction within the subsurface formation that results in any change in temperature, an understanding of degradation of LNAPL in an impacted area may be obtained. For example, FIG. 4 is a graph 400 of measured and estimated natural source zone depletion (NSZD) rate in a light non-aqueous phase liquids-impacted area determined from the methods and systems discussed herein. In particular, the graph 400 illustrates example latitude (y-axis 402) and longitude (x-axis 404) coordinates. A mapping of NSZD rate (in gallons per acre per year) of the example geographic area is illustrated based on measurements and calculations obtained from monitoring sites 406 (illustrated in the graph 400 as dots). One or more contour lines 408 at particular NSZD values may be included in the graph 400 to illustrate determined boundaries for varying NSZD rates. In some instances, a heat map coloring or other indicator may also be included in the graph 400 to illustrate a relationship between the contour lines 408 of the NSZD rates. The areas between monitoring sites 406 may, in some instances, be extrapolated from the data received at each monitoring site. In other words, the NSZD rates of the areas between the monitoring sites 406 may be estimated from the measured and determined NSZD rates at the monitoring sites 406 to provide the displayed indicators of the graph 400, including contour lines 408 and/or the heat map coloring of the graph.

In one instance, the graph 400 of FIG. 4 may be displayed on a display device of the computing device 128. For example, the NSZD rates of a particular geographic region may be obtained over a period of time utilizing the systems and methods discussed herein and graphed by the computing device 128. A graph of the NSZD rates, such as that illustrated in FIG. 4, may be displayed on the display device. Based on the displayed information or graphs, one or more remedial actions may be determined for the geographic regions. For example, areas with high NSZD rates may be identified by the computing device 128 as areas containing high volumes of subsurface pollutants. One or more remedial actions to remove the pollutants may be ordered or begun in response to the display of the graph 400. Such remedial actions may be formulated to remove the pollutants or other organic material from the subsurface region to achieve a site-specific goal of the organic material for the geographic region. In another example, the NSZD rates over many years may be monitored and graphed to illustrate areas in which subsurface pollutants have dissipated such that development of geographic areas may begin.

Figure 5:
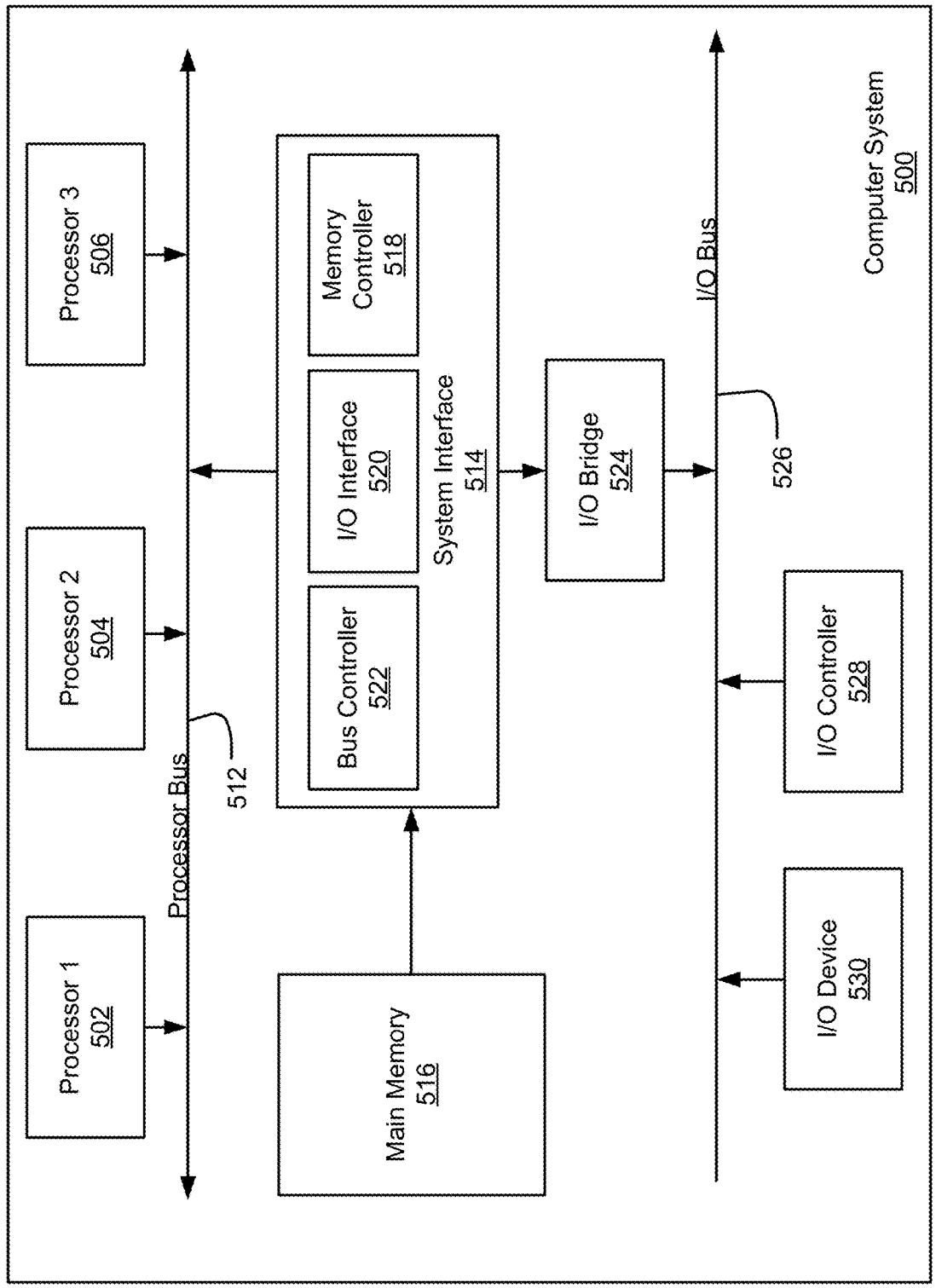
FIG. 5 is a diagram illustrating an example of a computing system which may be used in implementing embodiments of the present disclosure.

FIG. 5 is a block diagram illustrating an example of a computing device or computer system 500 which may be used in implementing the embodiments of the subsurface monitoring devices disclosed above. For example, the computing system 500 of FIG. 5 may be the computing device 128 discussed above. The computer system (system) 500 includes one or more processors 502-506. Processors 502-506 may include one or more internal levels of cache (not shown) and a bus controller or bus interface unit to direct interaction with the processor bus 512. Processor bus 512, also known as the host bus or the front side bus, may be used to couple the processors 502-506 with the system interface 514. System interface 514 may be connected to the processor bus 512 to interface other components of the system 500 with the processor bus 512. For example, system interface 514 may include a memory controller 514 for interfacing a main memory 516 with the processor bus 512. The main memory 516 typically includes one or more memory cards and a control circuit (not shown). System interface 514 may also include an input/output (I/O) interface 520 to interface one or more I/O bridges or I/O devices with the processor bus 512. One or more I/O controllers and/or I/O devices may be connected with the I/O bus 526, such as I/O controller 528 and I/O device 530, as illustrated.

I/O device 530 may also include an input device (not shown), such as an alphanumeric input device, including alphanumeric and other keys for communicating information and/or command selections to the processors 502-506. Another type of user input device includes cursor control, such as a mouse, a trackball, or cursor direction keys for communicating direction information and command selections to the processors 502-506 and for controlling cursor movement on the display device.

System 500 may include a dynamic storage device, referred to as main memory 516, or a random access memory (RAM) or other computer-readable devices coupled to the processor bus 512 for storing information and instructions to be executed by the processors 502-506. Main memory 516 also may be used for storing temporary variables or other intermediate information during execution of instructions by the processors 502-506. System 500 may include a read only memory (ROM) and/or other static storage device coupled to the processor bus 512 for storing static information and instructions for the processors 502-506. The system set forth in FIG. 5 is but one possible example of a computer system that may employ or be configured in accordance with aspects of the present disclosure.

According to one embodiment, the above techniques may be performed by computer system 500 in response to processor 504 executing one or more sequences of one or more instructions contained in main memory 516. These instructions may be read into main memory 516 from another machine-readable medium, such as a storage device. Execution of the sequences of instructions contained in main memory 516 may cause processors 502-506 to perform the process steps described herein. In alternative embodiments, circuitry may be used in place of or in combination with the software instructions. Thus, embodiments of the present disclosure may include both hardware and software components.

A machine readable medium includes any mechanism for storing or transmitting information in a form (e.g., software, processing application) readable by a machine (e.g., a computer). Such media may take the form of, but is not limited to, non-volatile media and volatile media and may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory devices 506 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in main memory 516, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

Embodiments of the present disclosure include various steps, which are described in this specification. The steps may be performed by hardware components or may be embodied in machine-executable instructions, which may be used to cause a general-purpose or special-purpose processor programmed with the instructions to perform the steps. Alternatively, the steps may be performed by a combination of hardware, software and/or firmware.

It should be understood from the foregoing that, while particular aspects have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A system for monitoring subsurface conditions, the system comprising:
   a first thermal sensor in communication with a data logger, the first thermal sensor transmitting, to the data logger, at least one obtained temperature at a first subsurface location;
   a second thermal sensor in communication with the data logger, the second thermal sensor transmitting, to the data logger, at least one obtained temperature at a second subsurface location; and
   a computing device in communication with the data logger, the computing device comprising at least one hardware processor and at least one memory to store executable instructions that, when executed by the at least one processor, are configured to:
   estimate a planar location of a subsurface heating or cooling source produced by an endothermic reaction or an exothermic reaction of organic; material within a subsurface formation;
   calculate, utilizing the least one obtained temperature at the first subsurface location, the least one obtained temperature at the second subsurface location, and the estimated planar location of the subsurface heating or cooling source, a first thermal parameter corresponding to an estimated rate of thermal change of a surface heating or cooling source and a second thermal parameter corresponding to an estimated rate of thermal change of the subsurface heating or cooling source at the estimated planar location of the subsurface heating or cooling source;
   calculate, utilizing the first thermal parameter, the second thermal parameter, and the estimated planar location of the subsurface heating or cooling source, an estimated temperature distribution within the subsurface formation corresponding to a rate of change of an amount of the organic material within the subsurface formation; and
   initiate a site remedy action for remediation of the subsurface formation based on the rate of change of the amount of the organic material within the subsurface formation.

2. The system of claim 1 wherein the second subsurface location is aligned vertically with the first subsurface location.

3. The system of claim 2 further comprising:
   a plurality of additional thermal sensors, each of the plurality of additional thermal sensors in communication with the data logger and to obtain at least one temperature at a corresponding subsurface location.

4. The system of claim 3 further comprising:
   a vertical structure supporting the first thermal sensor, second thermal sensor, and the plurality of additional thermal sensors in a vertical arrangement in the subsurface formation.

5. The system of claim 1, wherein the executable instructions are further configured to:
   calculate, utilizing the least one obtained temperature at the first subsurface location, the least one obtained temperature at the second subsurface location, and the estimated planar location of the subsurface heating or cooling source, an expected temperature distribution within the subsurface formation.

6. The system of claim 5, wherein the executable instructions are further configured to:
   obtain a set of obtained temperatures from the plurality of additional thermal sensors; and correlate each of the set of obtained temperatures to a corresponding subsurface location.

7. The system of claim 6, wherein the executable instructions are further configured to:
   compare the set of obtained temperatures to the expected temperature distribution within the subsurface formation; and
   generate, based on the comparison, a comparison value comprising a calculated difference between the set of obtained temperatures and the expected temperature distribution.

8. The system of claim 7, wherein the executable instructions are further configured to:
   adjust, in response to the comparison value exceeding an allowable tolerance value, the estimated planar location of the subsurface heating or cooling source.

9. The system of claim 1, wherein the computing device further comprises a display device, the executable instructions further configured to:
   display on the display device a visual representation of the rate of change of the amount of the organic material.

10. The system of claim 9, wherein the visual representation of the rate of change of the amount of the organic material comprises a rate of change of the amount of the organic material over a period of time.

11. The system of claim 1, wherein the site remedy action for remediation of the subsurface formation comprises removing an amount of the organic material within the subsurface formation.

12. A method for monitoring subsurface conditions, the method comprising:
   obtaining, from a first thermal sensor at a first subsurface location, a first temperature measurement and, from a second thermal sensor at a second subsurface location vertically aligned with the first subsurface location in a single data collection location, a second temperature measurement;
   estimating, via a processor of a computing device executing one or more instructions, a planar location of a subsurface heating or cooling source produced by an endothermic reaction or an exothermic reaction of organic material within a subsurface formation;
   calculating, via the processor executing the one or more instructions and without correcting for background temperature, a first thermal parameter corresponding to an estimated rate of thermal change of a surface heating or cooling source and a second thermal parameter corresponding to an estimated rate of thermal change due to the subsurface heating or cooling source at the estimated planar location of the subsurface heating or cooling source, the first thermal parameter and the second thermal parameter based on the obtained first temperature and the obtained second temperature;
   calculating, via the processor executing the one or more instructions and utilizing the first thermal parameter, the second thermal parameter, and the estimated planar location of the subsurface hearing or cooling source, an estimated temperature distribution within the subsurface formation corresponding to a rate of change of an amount of the organic material within the subsurface formation; and initiating a site remedy action for remediation of the subsurface formation based on the rate of change of the amount of the organic material within the subsurface formation.

13. The method of claim 12 further comprising:
obtaining, from a plurality of additional thermal sensors, a plurality of additional temperature measurements, each additional temperature measurement corresponding to a separate subsurface location between the first subsurface location and the second subsurface location in the single data collection location.

14. The method of claim 13 further comprising:
storing, in a database in communication with the computing device, the plurality of additional temperature measurements and the corresponding separate subsurface location.

15. The method of claim 14 further comprising:
calculating, via the processor executing the one or more instructions and utilizing the obtained first temperature, the obtained second temperature, and the estimated planar location of the subsurface heating or cooling source, an expected distribution of temperature within the subsurface formation provided by the surface heating or cooling source and the subsurface heating or cooling source.

16. The method of claim 15 further comprising:
comparing, via the processor executing the one or more instructions, the plurality of additional temperature measurements to the expected distribution of temperature within the subsurface formation; and
generating, based on the comparison, a comparison value comprising a calculated difference between the plurality of additional temperature measurements and the expected distribution of temperature within the subsurface formation.

17. The method of claim 16 further comprising:
adjusting, via the processor executing the one or more instructions and in response to the comparison value exceeding an allowable tolerance value, the estimated planar location of the subsurface heating or cooling source.

18. The method of claim 12 further comprising:
displaying, on the display device in communication with the computing device, a visual representation of the rate of change of the amount of the organic material.

19. The method of claim 18, wherein the visual representation of the rate of change of the amount of the organic material comprises a rate of change of the amount of the organic material over a period of time.

20. The method of claim 12, wherein the site remedy action for remediation of the subsurface formation comprises removing an amount of the organic material within the subsurface formation.

* * * * *